United States Patent
Choi et al.

(10) Patent No.: US 9,855,365 B2
(45) Date of Patent: Jan. 2, 2018

(54) PRODUCTION METHOD FOR BIOMEDICAL AND INDUSTRIAL MATERIAL USING CERAMIC DERIVED FROM BIRDS' BEAKS

(71) Applicants: CHUNGBUK NATIONAL UNIVERSITY INDUSTRY-ACADEMIC COOPERATION FOUNDATION, Cheongju-si (KR); KYUNGPOOK NATIONAL UNIVERSITY INDUSTRY-ACADEMIC COOPERATION FOUNDATION, Daegu (KR); INDUSTRY FOUNDATION OF CHONNAM NATIONAL UNIVERSITY, Gwangju (KR)

(72) Inventors: Seok Hwa Choi, Cheongju-si (KR); Jun Sik Son, Gwangju (KR); Seong Soo Kang, Gwangju (KR); Chang Ho Lee, Gwangju (KR)

(73) Assignees: Chungbuk National University Industry-Academic Cooperation Foundation, Cheongju-si, Chungcheongbuk-do (KR); Kyungpook National University Industry-Academic Cooperation Foundation, Daehak-ro, Buk-gu, Daegu (KR); Industry Foundation of Chonnam National University, Yongbong-ro, Buk-gu, Gwangju (KR)

( * ) Notice: Subject to any disclaimer, the term of this patent is extended or adjusted under 35 U.S.C. 154(b) by 224 days.

(21) Appl. No.: 14/360,169

(22) PCT Filed: Nov. 23, 2012

(86) PCT No.: PCT/KR2012/009977
§ 371 (c)(1),
(2) Date: May 22, 2014

(87) PCT Pub. No.: WO2013/077669
PCT Pub. Date: May 30, 2013

(65) Prior Publication Data
US 2015/0165090 A1    Jun. 18, 2015

(30) Foreign Application Priority Data
Nov. 23, 2011 (KR) .................. 10-2011-0122754

(51) Int. Cl.
*A61L 27/12* (2006.01)
*C04B 35/447* (2006.01)
(Continued)

(52) U.S. Cl.
CPC ............ *A61L 27/12* (2013.01); *A61L 27/18* (2013.01); *A61L 27/3608* (2013.01);
(Continued)

(58) Field of Classification Search
CPC ...................................... A61L 27/12
See application file for complete search history.

(56) References Cited

U.S. PATENT DOCUMENTS 5,167,961 A * 12/1992 Lussi .................. A61L 27/3608
424/422
5,691,397 A * 11/1997 Glimcher ................ A61L 24/02
264/344
(Continued)

FOREIGN PATENT DOCUMENTS

WO    WO-2008/032928 A1    3/2008

OTHER PUBLICATIONS

International Search Report for International Patent Application No. PCT/KR2012/009977, dated Mar. 3, 2013 (5 pages).
(Continued)

Primary Examiner — Michael Pepitone

(74) *Attorney, Agent, or Firm* — Clark & Elbing LLP; Susan M. Michaud

(57) ABSTRACT

The present invention relates to a method for preparing a ceramic powder from a bone of a bird's beak, a method for preparing biomedical or industrial ceramic materials by using the ceramic powder derived from a bone of a bird's beak, and a biomedical or industrial ceramic material prepared by the method thereof. The use of the present ceramic powder for manufacturing biomedical or industrial ceramic materials is safer than the use of the ceramic powder derived from allogenic bone or xenogeneic bone. In addition, the ceramic powder of the present invention can be prepared on a mass production basis. Furthermore, the ceramic material prepared using the ceramic powder of the present invention is more biocompatible than that prepared using artificially synthetic ceramic.

14 Claims, 4 Drawing Sheets

(51) Int. Cl.

| | |
|---|---|
| *C04B 35/622* | (2006.01) |
| *A61L 27/36* | (2006.01) |
| *C04B 35/111* | (2006.01) |
| *C04B 35/486* | (2006.01) |
| *C04B 35/626* | (2006.01) |
| *C04B 35/634* | (2006.01) |
| *C04B 38/06* | (2006.01) |
| *C04B 35/64* | (2006.01) |
| *A61L 27/46* | (2006.01) |
| *A61L 27/18* | (2006.01) |
| *C04B 111/00* | (2006.01) |

(52) U.S. Cl.
CPC ............ *A61L 27/46* (2013.01); *C04B 35/111* (2013.01); *C04B 35/447* (2013.01); *C04B 35/486* (2013.01); *C04B 35/62204* (2013.01); *C04B 35/62218* (2013.01); *C04B 35/62231* (2013.01); *C04B 35/62645* (2013.01); *C04B 35/62655* (2013.01); *C04B 35/634* (2013.01); *C04B 35/64* (2013.01); *C04B 38/0615* (2013.01); *A61L 2430/02* (2013.01); *C04B 2111/00836* (2013.01); *C04B 2235/3208* (2013.01); *C04B 2235/3212* (2013.01); *C04B 2235/3244* (2013.01); *C04B 2235/36* (2013.01); *C04B 2235/447* (2013.01); *C04B 2235/5252* (2013.01); *C04B 2235/5256* (2013.01); *C04B 2235/5427* (2013.01); *C04B 2235/5436* (2013.01); *C04B 2235/5445* (2013.01); *C04B 2235/5454* (2013.01); *C04B 2235/604* (2013.01)

(56) References Cited

U.S. PATENT DOCUMENTS

2008/0069852 A1\* 3/2008 Shimp ................... A61L 27/446
424/423
2009/0304807 A1\* 12/2009 Rhee ..................... A61F 2/4644
424/549

OTHER PUBLICATIONS

Aerssens et al., "Interspecies differences in bone composition, density, and quality: potential implications for in vivo bone research," Endocrinology. 139(2):633-70 (1998).
Sik Son et al., "Preliminary evaluation of bone graft substitute produced by bone of duck beak," Materials Letters. 121:181-4 (2014).

\* cited by examiner

PRODUCTION METHOD FOR BIOMEDICAL AND INDUSTRIAL MATERIAL USING CERAMIC DERIVED FROM BIRDS' BEAKS

CROSS-REFERENCE TO RELATED APPLICATIONS

This application is the U.S. National Phase of International Patent Application No. PCT/KR2012/009977, filed Nov. 23, 2012, which claims priority from Korean Patent Application No. 10-2011-0122754, filed on Nov. 23, 2011, in the Korean Intellectual Property Office.

FIELD OF THE INVENTION

The present invention relates to a method of preparing ceramic raw materials from a bone of a bird's beak, a method of preparing the biomedical or industrial ceramics from the ceramic raw materials derived from a bone of a bird's beak, and biomedical or industrial ceramics prepared from the method thereof.

DESCRIPTION OF THE RELATED ART

Biomedical ceramics are widely used today in the medical fields such as dental surgery, orthopaedics, and plastic surgery for treating or repairing the bone loss or damage because of their superior mechanical properties and biocompatibilities compared to the polymer materials. Ceramics are commonly subdivided into oxide ceramics and non-oxide ceramics. A group of ceramics of calcium phosphate, bioactive glass, alumina, zirconia, and complex thereof are widely utilized for the biomedical applications. The calcium phosphate ceramics includes hydroxyapatite (HA), tricalcium phosphate (TCP), tetracalcium phosphate (TTCP) and dicalcium phosphate (DCP), and the bioactive glass comprises silica-based glasses, phosphate-based glasses and glass ceramics. Bioceramics can be obtained from various sources such as bones of human, animal and fish, shell of clams and squid, coral, and egg shells. Among them, ceramics obtained from the bones of human and animal are now employed for the regeneration of human bone after having been processed with diverse treatments. In particular, most widely used calcium phosphate ceramic is hydroxyapatite (HA) which also occupies the greater part of the human bone constituent and whose molar ratio of calcium to phosphorus varies from 1.2 to almost 2 that is very similar to that of human bone. In addition, it is known that hydroxyapatite (HA) has such an excellent bio-activities that it can facilitate the adhesion, migration, and proliferation of cells and thus has an outstanding osteoconductivity and biocompatibility.

Currently, for the treatment or regeneration of the damaged human bone, xenograft using ceramic materials derived from xenogeneic bone such as bovine or porcine bone is frequently utilized, however, drawbacks of immune rejection, transmission of animal disease into human, and supply limitation were brought up and especially xenograft using bovine bone material is not free from the issue of bovine spongiform entephalopathy. Allograft using ceramic materials derived from allogenic bone that is other person's bone (e.g. receiving a bone donation from a dead person) is relatively excellent in substitution effect, however, the possibility of the disease transmission, problem of unidentified bone donor, and shortage of available bone source aggravate the psychological burden of the recipient. Autograft using ceramic materials derived from autogenic bone is most excellent in view of bone regeneration, however, there are demerits of indispensable secondary additional operation and supply limitation. Although artificially synthesized bone is cheap and is free from disease transmission and immune rejection, it has highly controversial issue because problems of slow bone regeneration, low quality of regenerated bone, and irritation at and around the transplanted region due to the non-adsorption or over-adsorption rate were reported and the bone healing effect is significantly low. Hydroxyapatite ceramics are utilized for various industrial application fields, for example filter materials in the water purifier to adsorb bacteria, photocatalysts, materials for fabricating industrial fiber & non-woven fabric, cement, paint, adhesive, a reinforcing agent, aggregate, and heavy metal absorbent materials. In addition, it is widely used for preparing cosmetics, and tooth paste.

Over the past few years, researches in the field of biomedical ceramics have been mainly focused on the development of bone graft materials which are in the form of block or particle and high porosity with internal pores being interconnected with each other. As a result of those researching efforts, porous ceramics can be prepared by using the method of particles leaching [B. Flautre et al, J Mater Sci Mater Med, 12, 679-682 (2001)], method of liquid nitrogen [Hone et al, J Mater Sci Mater Med, 22, 349-355 (2011)], method of bubble formation [Li et al, J Biomed Mater Res, 61, 109-120 (2002)], method of polymer sponge template [Appleford et al, Biomaterials, 28, 4788-4794 (2007)] and method of prototyping using CAD (computer aided design) system [Rumpler et al, J Biomed Mater Res, 81A, 40-50 (2007)]. Recently, researches are also focused on the biomedical materials consisting of organic-inorganic composites (or hybrid) combined with biodegradable polymer for the implantable use. In addition, an effort to develop a method for manufacturing industrially applicable nanoparticles from HA or other ceramics is now made and it can be expected to obtain an improved functionality owing to having a wide surface area ratio to volume when nanoparticles are used in the industrial field.

Up to recent times, although outstanding achievements have been made in the physical properties of biomedical materials, industrial materials, and organic-inorganic composites, however researches to develop ceramic materials that can be obtained from new natural sources have not been made hitherto. Especially, it is now a crucial point to develop bio-ceramics which is derived from a new natural source and applicable more safely to human body compared to the ceramics currently used. In addition, it is also important to develop a method for preparing ceramic raw materials which have a competitive price with mass production.

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THIS INVENTION

Technical Purposes of this Invention

The present inventors have made intensive studies to solve the above mentioned problems and as a result have finally developed a method for biomedically and industrially applicable ceramics from the ceramic powder of a bone of a bird's beak. The inventors are convinced that the instant ceramics can be used more safely than allograft or xenograft and can be mass-produced with low cost compared with autograft and have superior biocompatibility compared to artificially synthesized ceramics.

Accordingly, it is an object of this invention to provide a method of preparing a ceramic powder from a bone of a bird's beak.

It is another object of this invention to provide a method of preparing biomedical or industrial ceramic materials using ceramic powder derived from a bone of a bird's beak.

It is still another object of this invention to provide biomedical or industrial ceramic materials made of ceramic powder derived from a bone of a bird's beak.

Other objects and advantages of the present invention will become apparent from the following detailed description together with the appended claims and drawings.

DETAILED DESCRIPTION OF THIS INVENTION

Figure 1:
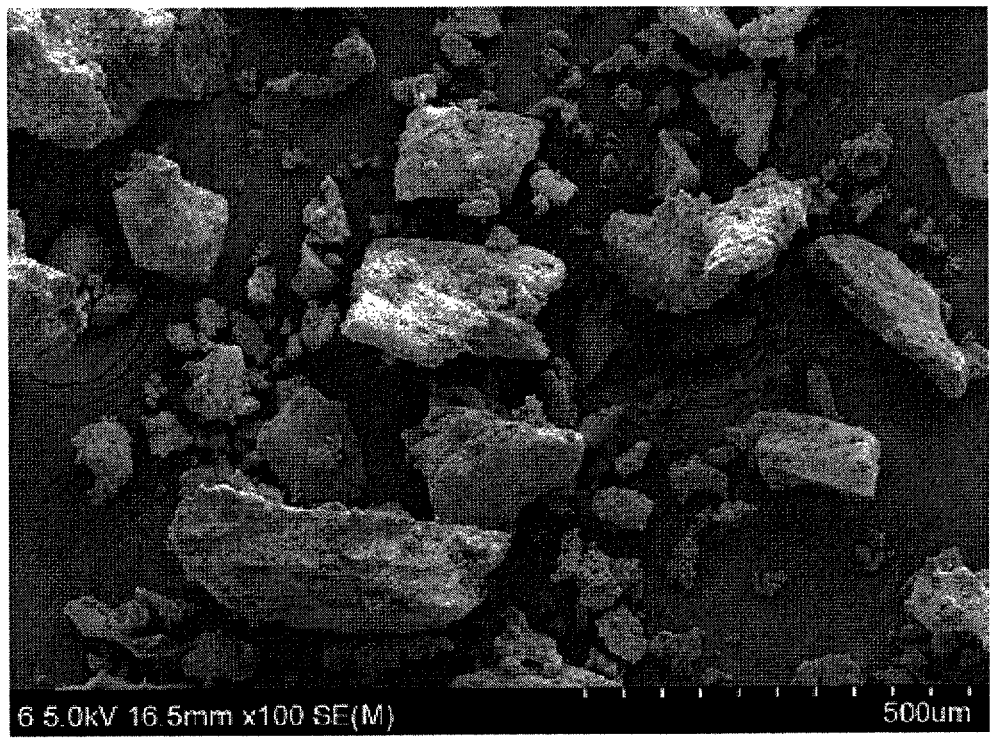
FIG. 1 represents scanning electron microscope (SEM) photograph of the particles of ceramic powder prepared from a bone of a duck's beak in accordance with the method described in the example 1.

In one aspect of this invention, there is provided a method for preparing a ceramic powder from a bone of a bird beak, which comprises the steps of: (a) retrieving a bone from a bird's beak; and (b) preparing ceramic powder by pulverizing the retrieved bone of the bird's beak.

The present invention is described in more detail according to the specific steps of the process of the instant method hereinafter.

Step (a): Retrieving a Bone from a Bird's Beak

The bird that can be used in the instant invention comprises any bird which has a beak containing a bone. Preferably, the bird may be any one that can be mass raised comprising for example, an egg breed bird, a meat breed bird, an egg and meat combined breed bird, a medicinal breed bird, an ornamental bird, a pet bird, a bird for fighting. Preferably, the bird may be poultry. According to a preferred embodiment, the bird comprises a duck, a goose, a turkey, a chicken, a pheasant, a quail, and an ostrich.

The duck comprises ducks having a bone of a beak for example tree ducks, shelducks, surface-feeding ducks, diving ducks, or mergansers; an egg bread duck of Indian runner or Khaki Cambell; a meat breed duck of Rouen, Aylesbury, Muscovy; an egg and meat combined breed duck of Pekin, Orpington, sulfur duck, Chinese merganser, surf duck, wood duck, Canadian goose; and mixed species thereof.

The goose comprises Toulouse goose, African goose, Embden goose, Chinese goose and mixed species thereof.

Turkey comprises a bronze turkey, a large white turkey, a small white turkey and mixed species thereof.

Chicken comprises oriental origin chickens of bragma, coohin, langshan, malay, Korean Ogol Chicken (Silkies); American origin chickens of Plymouth rock, Rhode Island, N.H., Wyandotte; English origin chickens of Australop, Cornish, Andalusina, Ancona, Spanish; an egg breed chicken of Leghorn, Minorca, Andalusian, Hamburgh, Compine, Ancona; an meat breed chicken of Brahma, cochin cornich; a pet chicken of Polish and Bantam; and mixed species thereof.

Retrieving a beak containing a bone from a bird can be carried out by using a cutting instrument such as saw or a knife but not limited to. When retrieving a bird's beak containing a bone, it is preferable that any heterologous material such as meat or hair is not included in the bird beak. The age and size of the bird from which the bone of bird beak is obtained is not particularly limited but it is preferable the bird is such a large one to get a bird beak containing a bone.

According to a preferred embodiment, the method of the present invention further comprises a step of removing a heterologous substance remained in the bone of the bird's beak after retrieving it from a bird. The heterologous substance may be an organic material such as a protein, an oil, and natural coloring matter. Removing the heterologous substance can be carried out by (i) the treatment with the chemical reagents or (ii) heat treatment.

The chemical reagents used for removing the heterologous substance can be selected from the group consisting of an aqueous solution of a hydrogen peroxide, urea hydrogen peroxide, sodium percarbonate, a compound containing hydrogen peroxide and a mixture thereof. Preferably, the chemical reagent for removing the heterologous substance is an aqueous solution of a hydrogen peroxide. The content of a hydrogen peroxide in the aqueous solution is 1-80 vol %, more preferably 2-70 vol %, still more preferably, 2-60 vol %, and most preferably 3-50 vol %. The treatment with the aqueous solution of a hydrogen peroxide can be performed for 1-72 hours under the temperature of 4-100° C., more preferably for 1-24 hours under the temperature of 10-90° C. When treating with the hydrogen peroxide, further treatments with ultrasonic waves, a catalase, a sodium carbonate, or a sodium sulfate can be added in order to accelerate the decomposition activity of the hydrogen peroxide.

Furthermore, the chemical reagent used for removing the heterologous substance includes an organic compound containing add or base. An oil or protein remained in the bone of bird's beak can be removed by the treatment with acid or base.

In addition to the treatment with a chemical reagent, the heterologous substance remained in the bone of the bird's beak can be removed by applying a heat to the bone of the bird's beak. The heat treatment can be carried out under the temperature of 200-1500° C. for 1-24 hours, more preferably under the temperature of 300-1300° C. for 1-5 hours.

Step (b): Preparing Ceramic Powder by Pulverizing the Retrieved Bone of the Bird's Beak.

The retrieved bone of the bird's beak, in which a heterologous substance of an organic material has been removed, can be pulverized by a physical method. For example, the bone of the bird's beak can be pulverized by using a grinder. The particle size of the ceramic powder made by pulverizing the bone of the bird's beak may be varied according to its application site in the human body or its industrial use. The size of the ceramic powder particle can be controlled by regulating the condition of the grinder. The diameter of the ceramic powder particle is preferably in the range of 100 nm-1 cm, more preferably is in the range of 400 nm-500 µm.

The ceramic powder prepared according to the method of the present invention from the bone of the bird's beak can be further passed through a demineralization process when it is used for a biomedical use. The chemical reagent used for the demineralization process can be selected from the group consisting of nitric acid, sulfuric acid, hydrochloric add, phosphoric acid, and mixture thereof. According to a preferred embodiment, the demineralization process can be carried out by immersing the ceramic powder into the solution containing 5-50 vol % of the chemical reagent for 1-24 hours.

In another aspect of this invention, there is provided a method for preparing biomedical or industrial ceramic materials which comprises the steps of: (a) preparing a ceramic powder from a bone of a bird's beak by using the present method; and (b) forming ceramic materials by using (i) the ceramic powder derived from a bone of a bird's beak or (ii) mixture of the ceramic powder derived from a bone of a bird's beak and heterologous ceramic powder.

The term "biomedical" used herein means the use of the present ceramic materials for transplantation into the human body, which have the properties of biostability and biocompatibility.

The term "industrial" used herein means the use of the present ceramic materials for preparing an apparatus or instrument which is not implanted into the human body, for example the apparatus or instrument includes filter, photocatalyst, fiber, nonwoven fabrics, cement, paint, adhesive, reinforcing agent, aggregate, heavy metal absorbent, cosmetics, toothpaste, and clothing fiber.

Biomedical or industrial ceramic materials can be prepared by using the ceramic powder derived from a bone of a bird's beak. At this time, the ceramic materials can be also prepared by using the mixture powder of the ceramic powder derived from a bone of a bird's beak with the heterologous ceramic powder.

The heterologous ceramic powder that can be used in the present invention is a naturally occurring ceramic powder or an artificially synthetic ceramic powder. For example, the naturally occurring ceramic may be the one which is derived from allogeneic bone, xenogeneic bone or autogenous bone. The artificially synthetic ceramic may be the one or more selected from the group consisting of calcium phosphate ceramics, bioactive galss, alumina, zirconia, and complex thereof. The calcium phosphate ceramics include for example hydroxyapatite (HA), dicalcium phosphate (DCP), tricalcium phosphate (TCP), and tetracalcium phosphate (TTCP). The bioactive glass refers to any glass having the property of biocompatibility or to an amorphous solid material capable of forming a cohesive bond with the hard or soft tissue when exposed to an appropriate in vivo or in vitro condition such as a simulated body fluid or trihydroxymethylaminomethane buffer. Specifically, the bioactive glass includes silica based glasses, phosphate-based glasses, and glass ceramics. Most preferably, the artificially synthetic ceramic may be selected from the group consisting of hydroxyapatite (HA), dicalcium phosphate (DCP), tricalcium phosphate (TCP), tetracalcium phosphate (TTCP), zirconia, alumina, galss, silica/glass complex, silica/calcium phosphate ceramic complex, and complex thereof.

The content of the heterologous ceramic powder which is contained in the biomedical or industrial ceramic materials is not particularly limited but preferably is in the range of 1-99 wt %, more preferably in the range of 10-90 wt %.

According to a preferable embodiment, said step (b) of forming ceramic materials may be carried out by, but not limited to, methods of compression method, particle leaching method, liquid nitrogen method, bubble formation method, polymer spongy template method, or prototyping method using computer aided design (CAD).

According to another preferable embodiment, said step (b) of forming ceramic materials may further comprise a heat treatment process and the heat treatment process can be carried out under the temperature of 600-1500° C. for 1-3 hrs but not limited to this condition.

According to still another preferable embodiment, the step (b) may further comprise mixing a polymer with (i) the ceramic powder derived from a bone of a bird's beak or (ii) mixture of the ceramic powder derived from a bone of a bird's beak with the heterologous ceramic powder.

The polymer to be mixed can be selected from the group consisting of polyester, polyimide, polyether, aramide, polystyrene, polypropylene, polymethyl methacrylate, polyalkylene naphthalate, polyvinyl alcohol, acrylic resin, gum resin, phenolic resin, epoxy resin, teflon polymer, and copolymer thereof; polydioxanone, polyglycolic acid, polylactic acid, polycaprolactone, lactic acid-glycolic add copolymer, glycolic acid-trimethylcarbonate, glycolic acid-ϵ-caprolactone, polyglyconate, polyglactin, polyamino acid, polyanhydride, polyorthoester, mixture thereof, and copolymer thereof; collagen, gelatin, chitin/chitosan, alginate, albumin, hyaluronic acid, heparin, fibrinogen, cellulose, dextran, pectin, polylysine, and polyethyleneimine, but not limited to.

The mixing the polymer with the ceramic powder derived from a bone of a bird's beak or the mixture powder of the ceramic powder derived from a bone of a bird's beak and heterologous ceramic powder can be carried out by any proper method according to the properties of the polymer, for example by adding the ceramic powder or the mixture powder of the ceramic powders into the molten polymer or polymer solution.

The content of the polymer to be added into the ceramic powder may be preferably 1-99 wt %, and more preferably 10-90 wt % but not limited to.

The formation of the biomedical or industrial ceramic materials using the ceramic powder mixture with the polymer can be carried out the method selected from the group consisting of emulsification method, phase-separation method, solvent diffusion method, compression method, particle leaching method, liquid nitrogen method, bubble formation method, polymer spongy template method, solvent spinning method, melt spinning method, wet spinning method, air spinning method, melting molding method, solvent molding method, particle addition method, and prototyping method using computer aided design (CAD) but not limited to.

In still another aspect of this invention, there is provided a biomedical or industrial ceramic material, which comprises (i) a ceramic powder derived from a bone of a bird's beak; (ii) a mixture of a ceramic powder derived from a bone of bird beak with a heterologous ceramic powder; or (iii) a mixture of a polymer with said ceramic powder of (i) or (ii).

According to a preferred embodiment, the shape of the biomedical or industrial ceramic material can be selected from the group consisting of block, film, filament, fiber, membrane, mesh, woven fabrics, nonwoven fabrics, knit, granule, particle, plate, bolt, nut, nail and combination thereof, but not limited to.

According to another preferred embodiment, the biomedical or industrial ceramic material of the present invention may be a non porous material or porous material. The porous ceramic material may have 5-98% porosity and the diameter of the pore is in the range of 0.1 nm-5 mm.

The ceramic material of the present invention can be utilized as any biomedical ceramic material which is directly contactable to the live body tissue for the regeneration of the body tissue or treatment of the disease. For example, the ceramic material of the present invention can be used for a supporter for any form of tissues such as artificial bone, artificial joint, bone cement, jawbone, facial area small size bone, hear valve, blood vessel, implant, abutment, filler, coating material, bracket, core, post; fixation device for joint, bone, or backbone. Furthermore, the ceramic material of the instant invention can be utilized as drug delivery agent, vascular contrast media, micro-electromechanical systems, antimicrobial filler material, or ceramic materials for hybrid complex.

The ceramic material of the present invention can be utilized as industrial ceramic materials including water purifier filter materials for adsorption of bacteria, photocatalyst materials for relieving sick house syndrome, cosmetics, toothpaste, fiber for clothing or industrial use, non-woven fabric, cement, paint, adhesive, a reinforcing agent, aggregate, complex, and heavy metal absorbent materials but not limited to.

The ceramic material of the present invention can be prepared such that it may include pharmaceutical active agent such as dexamethasone, chondroithin sulfate, lysozyme, DNA, RNA, RGD peptide, lipid, growth factor, growth hormone, peptide medicine, protein medicine, anti-inflammatory analgesic drug, anti-cancer agent, anti-virus agent, sex hormone, antibiotics, antimicrobial agent, and combination thereof but not limited to.

ADVANTAGEOUS EFFECTS

The present invention relates to a method for preparing a ceramic powder from a bone of a bird's beak, a method for preparing biomedical or industrial ceramic materials by using the ceramic powder derived from a bone of a bird's beak, and a biomedical or industrial ceramic material prepared by the method thereof. The use of the present ceramic powder for manufacturing biomedical or industrial ceramic materials is safer than the use of the ceramic powder derived from allogenic bone or xenogeneic bone. In addition, the ceramic powder of the present invention can be prepared on a mass production basis. Furthermore, the ceramic material prepared using the ceramic powder of the present invention is more biocompatible than that prepared using artificially synthetic ceramic.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Preparation of a Ceramic Powder from a Bone of a Duck's Beak

Figure 2:
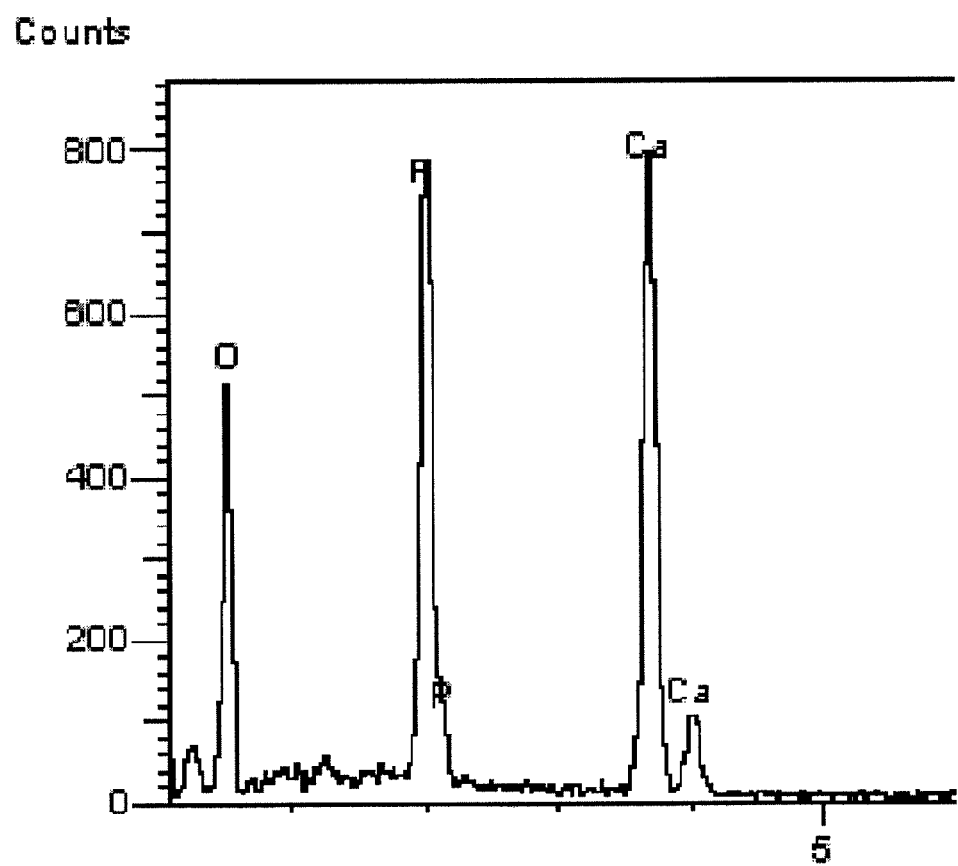
FIG. 2 shows the energy dispersive spectrometer (EDS) analysis profile as to the ratio of calcium to phosphate in the surface of ceramic powder particle prepared from a bone of a duck's beak in accordance with the method described in the example 1.

A bone was retrieved from a beak of a duck having a body weight of 1-3 kg and bleached by immersing in an aqueous solution of 10% hydrogen peroxide for 24 hrs. Afterwards, oil component remained on the bone was removed by immersing it in the solution of 1:1 (v/v) of chloroform: methanol for 24 hrs and eliminated the remained organic agent by washing with water several times. The protein components in the bone were removed by immersing it in the solution of 4% sodium hypochlorite and removed a remained sodium hypochlorite by washing with distilled water several times. The bone was completely dried through a freeze-drying process and then the organic materials remained in the dried bone were eliminated by the heat treatment under the temperature of 600° C. for 3 hrs. Then, the bone was pulverized into the powder having the particle with the diameter of 200-500 µm by using the grinder. The bone powder was washed through the process of immersing into the 100% acetone with applying the ultrasonic waves to it. The bone powder was further washed with distilled water for three times and then freeze-dried to result in the final ceramic powder derived from a bone of a duck's beak. In order to evaluate the morphological characteristics and stability of the particle in the ceramic powder prepared, an analysis by a scanning electron microscope (SEM) and an energy dispersive spectrometer (EDS) was carried out. FIG. 1 represents the scanning electron microscope (SEM) photograph and FIG. 2 shows the energy dispersive spectrometer (EDS) analysis profile. According to the results of SEM analysis as shown in FIG. 1, the average particle diameter of the ceramic powder is 300 µm. In addition, according to the results of the EDS analysis as shown in FIG. 2, the ratio of calcium to phosphate is 1:1.45, which is very similar to the ratio of calcium to phosphate in the bone of the human body. Furthermore, any peak representing foreign substances (e.g., heavy metal or salt) was not observed. As a result, it is verified that the ceramic powder obtained from a bone of a duck's beak in accordance with the present method is appropriate and stable for the application to the human body.

Example 2: Preparation of a Ceramic Powder from a Bone of a Chicken's Beak

Figure 3:
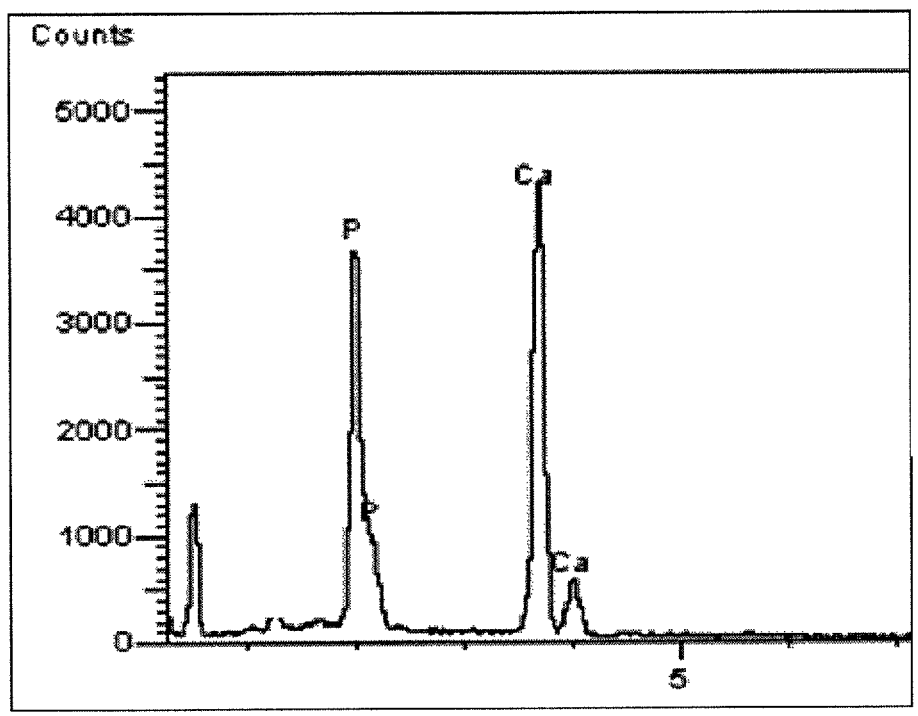
FIG. 3 shows the energy dispersive spectrometer (EDS) analysis profile as to the ratio of calcium to phosphate in the surface of ceramic powder particle prepared from a bone of a chicken's beak.

A bone was retrieved from a beak of a chicken having a body weight of 1-2 kg and bleached by immersing in an aqueous solution of 30% hydrogen peroxide having the temperature of 70° C. for 3 hrs. Afterwards, organic materials in the bone were removed by the heat treatment under the temperature of 1000° C. for 3 hrs. The bone was pulverized into the powder having the particle diameter of 50-20 µm by using the grinder. Then, the bone powder was washed through the process of immersing into the 100% acetone with applying the ultrasonic waves to it. The bone powder was further washed with distilled water for three times and then freeze-dried to finally result in a ceramic powder derived from a bone of chicken's beak. In order to evaluate the morphological characteristics and stability of the particle in the ceramic powder prepared, an analysis by a scanning electron microscope (SEM) and an energy dispersive spectrometer (EDS) was carried out. According to the results by an analysis with SEM and EDS, the characteristics of the particle in the powder obtained from a bone of a chicken's beak were very similar to those of Example 1. The result of the EDS analysis of the powder derived from a bone of a chicken's beak is shown in FIG. 3. It is demonstrated that the ceramic powder derived from a bone of a chicken's beak in accordance with the present method is also appropriate and stable for the application to the human body.

Example 3: Preparation of a Ceramic Powder from a Bone of a Goose's Beak

Figure 4:
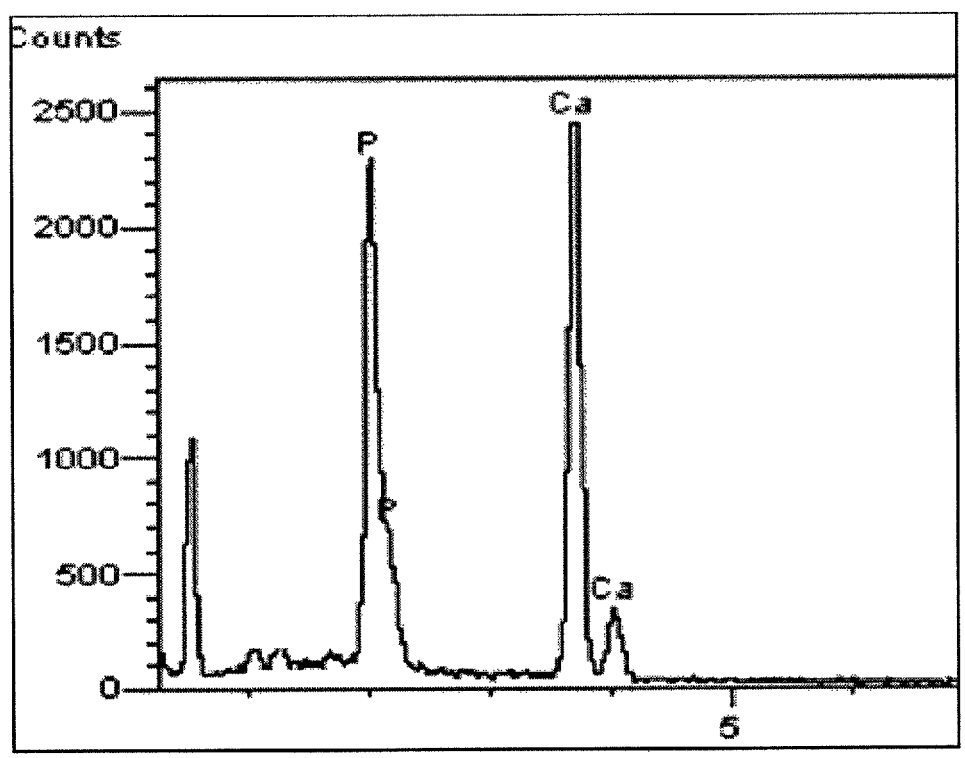
FIG. 4 shows the energy dispersive spectrometer (EDS) analysis profile as to the ratio of calcium to phosphate in the surface of ceramic powder particle prepared from a bone of a goose's beak.

A bone was retrieved from a beak of a goose having a body weight of 2-4 kg and bleached by immersing in an aqueous solution of 30% hydrogen peroxide having the temperature of 70° C. for 3 hrs. Afterwards, organic materials in the bone were removed by the heat treatment under the temperature of 1200° C. for 3 hrs. The bone was pulverized into the powder having the particle diameter of 500-900 μm by using the grinder. Then, the bone powder was washed through the process of immersing into the 100% acetone with applying the ultrasonic waves to it. The bone powder was further washed with distilled water for three times and then freeze-dried to finally result in a ceramic powder derived from a bone of goose's beak. In order to evaluate the morphological characteristics and stability of the particle in the ceramic powder prepared, an analysis by a scanning electron microscope (SEM) and an energy dispersive spectrometer (EDS) was carried out. According to the results by the analysis with SEM and EDS, the characteristics of the particle in the powder obtained from a bone of a goose's beak are very similar to those of Example 1. The result of the EDS analysis of the powder derived from a bone of a goose's beak is shown in FIG. 4. It is demonstrated that the ceramic powder derived from a bone of a goose's beak in accordance with the present method is appropriate and stable for the application to the human body.

Example 4: Preparation of a Porous Ceramic Complex Supporter from the Ceramic Powder Mixture of Hydroxyapatite and a Bone of a Duck's Beak Ceramic powder derived from a bone of a duck's beak was prepared in accordance with the method described in the example 1. The prepared ceramic powder was mixed with the powder of the synthetic ceramic, hydroxyapatite in the ratio of 50:50 wt %, and then 5 g of the mixed ceramic powder was added into 10 mL of an aqueous solution containing 3% polyvinyl alcohol and dispersed homogeneously in the solution with stirring for 24 hrs to finally result in ceramic slurry. Then, the temperature of the slurry was raised up to 50° C. to continuously evaporate 5 mL of water. After that, the prepared slurry was coated on a polyurethane spongy having 60 ppi (pore per inch), dried under the room temperature, and then applied to a heat treatment under the temperature of 1200° C. for 3 hrs to finally result in the porous ceramic complex supporter comprised of the mixed ceramic powder of hydroxyapatite and a bone of a duck's beak.

Example 5: Preparation of a Non-Porous Ceramic Complex Disc from the Ceramic Powder Mixture of Tricalcium Phosphate and a Bone of a Duck's Beak Ceramic powder derived from a bone of a duck's beak was prepared in accordance with the method described in the example 1. The prepared ceramic powder was mixed with the powder of the synthetic ceramic, tricalcium phosphate in the ratio of 50:50 wt %. After that, 1 g of the mixed ceramic powder was put into a cylindrical metal cast and compressed with the pressure of 5 MPa to make a disc shaped material, and then applied to a heat treatment under the temperature of 1200° C. for 3 hrs to finally result in the non-porous ceramic complex disc comprised of the mixed ceramic powder of tricalcium phosphate and a bone of a duck's beak.

Example 6: Preparation of a Porous Ceramic Complex Granule from the Ceramic Powder Mixture of Hydroxyapatite, Tricalcium Phosphate and a Bone of a Goose's Beak Ceramic powder derived from a bone of a goose's beak was prepared in accordance with the method described in the example 3. The prepared ceramic powder was mixed with the powder of the synthetic ceramics, hydroxyapatite and tricalcium phosphate in the ratio of 50:30:20 wt %. After that, the ceramic slurry was produced using the prepared mixed ceramic powder according to the same method described in the example 4. The slurry prepared was put into the syringe and dropped into liquid nitrogen through the hollow tip having a hole size of 18 G. The ceramic particle solidified in the liquid nitrogen was collected and freeze-dried, and then applied to a heat treatment under the temperature of 1100° C. to finally result in the porous ceramic complex granule comprised of the mixed ceramic powder from hydroxyapatite, tricalcium phosphate, and a bone of a duck's beak.

Example 7: Preparation of a Porous Ceramic Complex Supporter from the Ceramic Powder Mixture of Tricalcium Phosphate, Xenogeneic Bone and a Bone of a Duck's Beak Ceramic powder derived from a bone of a duck's beak was prepared in accordance with the method described in the example 1. Three kinds of powder, that is the prepared ceramic powder derived from a bone of a duck's beak, the ceramic powder prepared from a calf bone as a xenogeneic bone, and the tricalcium phosphate powder were mixed with the ratio of 30:30:40 wt %. After that, 5 g of the mixed ceramic powder was added into 10 mL of an aqueous solution containing 3% polyvinyl alcohol and dispersed homogeneously in the solution with stirring for 24 hrs to finally result in ceramic slurry. After that, the prepared slurry was coated on a polyurethane spongy having 80 ppi (pore per inch), dried under the room temperature for 24 hrs, and then applied to a heat treatment under the temperature of 1200° C. for 3 hrs to finally result in the porous ceramic complex supporter obtained from the mixed ceramic powder of tricalcium phosphate, xenogeneic bone and a bone of a duck's beak.

Example 8: Preparation of a Ceramic Complex Supporter from the Ceramic Powder Mixture of a Bone of a Duck's Beak and PLGA Polymer Ceramic powder derived from a bone of a duck's beak was prepared in accordance with the method described in the example 1. One gram of PLGA [poly(lactic-co-glycolic acid)] polymer was dissolved in 5 mL of dichloromethane, and 500 mg of the prepared ceramic powder was added into the solution, and then dispersed homogeneously with stirring. After that, the solution of the mixture was solidified by immersing into liquid nitrogen and freeze-dried to finally result in the ceramic complex supporter.

Example 9: Preparation of a Ceramic Complex Filament from the Ceramic Powder Mixture of a Bone of a Duck's Beak and PLA Polymer Ceramic powder derived from a bone of a duck's beak was prepared in accordance with the method described in the example 1. The polymer of PLA (poly lactic acid) was melted in the fiber spinning machinery by applying heat up to the temperature of 250° C. After that, the prepared ceramic powder was put into the extruder of the fiber spinning machinery, then mixed homogeneously, and spun through 1.0Φ extruding nozzle to finally result in the ceramic complex filament.

Example 10: Preparation of a Ceramic Complex Film from the Ceramic Powder Mixture of a Bone of a Duck's Beak and the PET Polymer Ceramic powder derived from a bone of a duck's beak was prepared in accordance with the method described in the example 1. Two grams of the polymer of polyethyleneterephthalate (PET) was completely dissolved in 2-chlorophenol and then 1 g of the prepared ceramic powder was put into the PET solution and dispersed homogeneously by stirring under the room temperature. The prepared solution of the mixture of PET and ceramic powder was poured into teflon mould for manufacturing film and vaporized completely away the solvent to finally result in the ceramic complex film.

Having described a preferred embodiment of the present invention, it is to be understood that variants and modifications thereof falling within the spirit of the invention may become apparent to those skilled in this art, and the scope of this invention is to be determined by appended claims and their equivalents.

ACKNOWLEDGEMENT

This research was supported by Bio-industry Technology Development Program, Ministry for Food, Agriculture, Forestry and Fisheries, Republic of Korea (312031-3).

What is claimed is:

1. A method for preparing a ceramic powder from a bone of a bird's beak, which comprises the steps of:
   (a) retrieving a bone from a bird's beak;
   (b) removing a heterologous substance remaining in the retrieved bone of the bird's beak; and
   (c) pulverizing the retrieved bone of the bird's beak into ceramic powder having a diameter of 400 um-500 um;
   wherein the ceramic powder from a bone of a bird's beak has a ratio of calcium to phosphate of 1:1.45.

2. The method according to claim 1, wherein the removal of the heterologous substance is carried out by (i) treatment with a chemical reagent selected from the group consisting of an aqueous solution of hydrogen peroxide, chloroform, methanol, sodium hypochlorite, and a mixture thereof, or (ii) heat treatment.

3. The method according to claim 2, wherein the treatment with the chemical reagent is carried out by immersing the bone from a bird's beak in an aqueous solution containing 1-80 vol % of the chemical reagent under the temperature of 4-100° C. for 1-72 hours.

4. The method according to claim 2, wherein the heat treatment is carried out under the temperature of 200-1500° C. for 1-24 hours.

5. The method according to claim 1, wherein the bird is selected from the group consisting of a duck, a goose, a turkey, a chicken, a pheasant, a quail, and an ostrich.

6. A method for preparing a biomedical or industrial ceramic material which comprises the steps of:
   (a) preparing a ceramic powder from a bone of a bird's beak by using the method according to claim 1; and
   (b) forming a ceramic material by the heat treatment of (i) the ceramic powder derived from a bone of a bird's beak or (ii) mixture of the ceramic powder derived from a bone of a bird's beak and a heterologous ceramic powder under the temperature of 600-1500° C. for 1-3 hours,
   wherein the ceramic material is a porous material having 5-98% porosity and the diameters of the pores of the ceramic material are in the range of 0.1 nm-5 mm.

7. The method according to claim 6, wherein the heterologous ceramic powder is a naturally occurring ceramic powder or an artificially synthetic ceramic powder.

8. The method according to claim 7, wherein the naturally occurring ceramic is derived from allogenic bone, xenogeneic bone or autogenous bone.

9. The method according to claim 6, wherein the artificially synthetic ceramic is selected from the group consisting of hydroxyapatite (HA), dicalcium phosphate (DCP), tricalcium phosphate (TCP), tetracalcium phosphate (TTCP), zirconia, alumina, glass, and mixture thereof.

10. The method according to claim 6, wherein step (b) further comprises adding a polymer into (i) the ceramic powder derived from a bone of a bird's beak, or (ii) the mixture of the ceramic powder derived from a bone of a bird's beak and the heterologous ceramic powder.

11. The method according to claim 10, wherein the polymer is selected from the group consisting of polyester, polyimide, polyether, aramide, polystyrene, polypropylene, polymethyl methacrylate, polyalkylene naphthalate, polyvinyl alcohol, acrylic resin, gum resin, phenolic resin, epoxy resin, teflon polymer, and copolymer thereof; polydioxanone, polyglycolic acid, polylactic acid, polycaprolactone, lactic acid-glycolic acid copolymer, glycolic aicd-trimethylcarbonate, glycolic acid-ϵ-caprolactone, polyglyconate, polyglactin, polyamino acid, polyanhydride, polyorthoester, mixture thereof, and copolymer thereof; collagen, gelatin, chitin/chitosan, alginate, albumin, hyaluronic acid, heparin, fibrinogen, cellulose, dextran, pectin, polylysine, and polyethyleneimine.

12. The method according to claim 6, wherein the formation of the ceramic material in step (b) is carried out by a method selected from the group consisting of emulsification method, phase-separation method, solvent diffusion method, compression method, particle leaching method, liquid nitrogen method, bubble formation method, polymer spongy template method, solvent spinning method, melt spinning method, wet spinning method, air spinning method, melting molding method, solvent molding method, particle addition method, and prototyping method using computer aided design (CAD).

13. A biomedical or industrial ceramic material, which comprises (i) a ceramic powder derived from a bone of a bird's beak; (ii) a mixture of a ceramic powder derived from a bone of a bird's beak and a heterologous ceramic powder; or (iii) a mixture of a polymer and said ceramic powder of (i) or (ii), wherein the ceramic material is a porous material having 5-98% porosity and the diameters of the pores of the ceramic materials are in the range of 0.1 nm-5 mm; the ceramic powder from a bone of a bird's beak has a ratio of calcium to phosphate of 1:1.45; and the ceramic material is prepared by the method according to claim 6.

14. The biomedical or industrial ceramic material according to claim 13, wherein the ceramic material is in a form selected from the group consisting of a block, film, filament, fiber, membrane, mesh, woven fabric, nonwoven fabric, knit, granule, particle, plate, bolt, nut, nail, and a combination thereof.

* * * * *